US011033493B2

(12) United States Patent
Obeid et al.

(10) Patent No.: US 11,033,493 B2
(45) Date of Patent: *Jun. 15, 2021

(54) FILM DOSAGE FORM WITH EXTENDED RELEASE MUCOADHESIVE PARTICLES

(71) Applicant: Intelgenx Corp., St-Laurent (CA)

(72) Inventors: Rodolphe Obeid, Pierrefonds (CA); Nadine Paiement, St-Laurent (CA); Erick Gonzalez-Labrada, Cote Saint-Luc (CA)

(73) Assignee: Intelgenx Corp., St. Laurent (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/110,737

(22) Filed: Aug. 23, 2018

(65) Prior Publication Data

US 2018/0360736 A1 Dec. 20, 2018

Related U.S. Application Data

(63) Continuation-in-part of application No. 15/588,897, filed on May 8, 2017, now Pat. No. 10,272,038, which is a continuation-in-part of application No. 14/554,332, filed on Nov. 26, 2014, now Pat. No. 9,668,970.

(60) Provisional application No. 61/910,604, filed on Dec. 2, 2013.

(51) Int. Cl.
| | |
|---|---|
| *A61K 9/00* | (2006.01) |
| *A61K 47/34* | (2017.01) |
| *A61K 47/32* | (2006.01) |
| *A61K 47/26* | (2006.01) |
| *A61K 47/36* | (2006.01) |
| *A61K 47/42* | (2017.01) |
| *A61K 47/20* | (2006.01) |
| *A61K 47/10* | (2017.01) |
| *A61K 47/12* | (2006.01) |
| *A61K 31/352* | (2006.01) |
| *A61K 36/185* | (2006.01) |
| *A61K 47/44* | (2017.01) |
| *A61K 45/06* | (2006.01) |
| *A61K 47/46* | (2006.01) |
| *A61K 31/05* | (2006.01) |

(52) U.S. Cl.
CPC .......... *A61K 9/006* (2013.01); *A61K 31/05* (2013.01); *A61K 31/352* (2013.01); *A61K 36/185* (2013.01); *A61K 45/06* (2013.01); *A61K 47/10* (2013.01); *A61K 47/12* (2013.01); *A61K 47/20* (2013.01); *A61K 47/26* (2013.01); *A61K 47/32* (2013.01); *A61K 47/34* (2013.01); *A61K 47/36* (2013.01); *A61K 47/42* (2013.01); *A61K 47/44* (2013.01); *A61K 47/46* (2013.01); *A61K 9/0065* (2013.01)

(58) Field of Classification Search
None
See application file for complete search history.

(56) References Cited

U.S. PATENT DOCUMENTS

| | | | |
|---|---|---|---|
| 5,180,578 A | 1/1993 | Gaffar et al. | |
| 5,334,375 A | 8/1994 | Nabi et al. | |
| 5,538,715 A | 7/1996 | Gaffar et al. | |
| 5,690,911 A | 11/1997 | Mirajkar et al. | |
| 6,596,298 B2 | 7/2003 | Leung et al. | |
| 6,923,981 B2 | 8/2005 | Leung et al. | |
| 7,025,983 B2 | 4/2006 | Leung et al. | |
| 7,407,669 B2 | 8/2008 | Leung et al. | |
| 7,867,509 B2 | 1/2011 | Leung et al. | |
| 8,137,713 B2 | 3/2012 | Boyd et al. | |
| 8,491,945 B2 | 7/2013 | Boyd et al. | |
| 8,642,080 B2 | 2/2014 | Bender et al. | |
| 9,668,970 B2 * | 6/2017 | Obeid | A61K 31/09 |
| 9,833,461 B2 | 12/2017 | Modi | |
| 10,272,038 B2 * | 4/2019 | Obeid | A61K 45/06 |
| 2002/0132008 A1 | 9/2002 | Mumper et al. | |
| 2002/0137728 A1 | 9/2002 | Montgomery | |
| 2005/0026819 A1 | 2/2005 | Kaniga | |
| 2006/0039959 A1 * | 2/2006 | Wessling | A61K 9/006 424/448 |

(Continued)

FOREIGN PATENT DOCUMENTS

| | | |
|---|---|---|
| CA | 2968929 | 6/2016 |
| CA | 2910206 | 12/2016 |

(Continued)

OTHER PUBLICATIONS

N Salamat-Miller, M Chittchang, TP Johnston. "The use of mucoadhesive polymers in buccal drug delivery." Advanced Drug Delivery Reviews, vol. 57, 2005, pp. 1666-1691. (Year: 2005).*
JO Morales, JT McConville. "Manufacture and characterization of mucoadhesive buccal films." European Journal of Pharmaceutics and Biopharmaceutics, vol. 77, 2011, pp. 187-199. (Year: 2011).*
Maria Laura Immordino, Franco Dosio, Luigi Cartel. "Stealth liposomes: review of the basic science, rationale, and clinical applications, existing and potential." International Journal of Nanomedicine 2006:1(3), pp. 297-315. (Year: 2006).*

(Continued)

*Primary Examiner* — Isaac Shomer
(74) *Attorney, Agent, or Firm* — Gunther J. Evanina; Butzel Long, PC

(57) ABSTRACT

An orally administered dosage form that facilitates delivery of an agent locally in the buccal cavity for a sustained period of time includes mucoadhesive particles that are made of at least a mucoadhesive material combined with the agent, and which are dispersed in a disintegrating film. The dosage form is capable of delivering an agent to a patient at the desired oral mucosa site over an extended period of time while reducing patient discomfort or annoyance associated with conventional sustained release mucoadhesive films that must reside on the oral mucosa during the period of sustained release.

20 Claims, No Drawings

(56) References Cited

U.S. PATENT DOCUMENTS

| | | |
|---|---|---|
| 2006/0140883 A1 | 6/2006 | Trivedi et al. |
| 2007/0224225 A1 | 9/2007 | Irache Garreta et al. |
| 2009/0124535 A1 | 5/2009 | Markland et al. |
| 2011/0028431 A1* | 2/2011 | Zerbe ............... A61P 11/06 514/58 |
| 2011/0293539 A1 | 12/2011 | Ibrahim et al. |
| 2011/0305768 A1* | 12/2011 | Mao ............... A61K 39/15 424/499 |
| 2012/0040010 A1 | 2/2012 | Harel et al. |
| 2012/0087944 A1 | 4/2012 | Tian et al. |
| 2012/0121669 A1 | 5/2012 | Fontana et al. |
| 2012/0121718 A1 | 5/2012 | Lai et al. |
| 2012/0288548 A1 | 11/2012 | Boyd et al. |
| 2015/0265720 A1 | 9/2015 | Levine et al. |
| 2015/0297531 A1* | 10/2015 | Ensign ............. A61K 9/5146 424/497 |
| 2016/0015683 A1* | 1/2016 | McCarty ............. A61K 31/05 206/528 |
| 2016/0051510 A1* | 2/2016 | Allen ............... A61K 31/366 424/443 |
| 2016/0228385 A1 | 8/2016 | Sievers et al. |
| 2017/0246120 A9 | 8/2017 | Stepovich |
| 2017/0252300 A1 | 9/2017 | Modi |
| 2017/0290870 A1* | 10/2017 | Schaneville ........ A61K 36/185 |
| 2017/1033338 | 11/2017 | Sarne |

FOREIGN PATENT DOCUMENTS

| | | | |
|---|---|---|---|
| CA | 2922959 | 1/2018 | |
| EP | 2298283 A2 * | 3/2011 | ........... A61K 9/0031 |
| WO | WO-2014145699 A1 | 9/2014 | |
| WO | WO-2016/092539 A1 | 6/2016 | |
| WO | WO-2016/103254 A1 | 6/2016 | |
| WO | WO-2017/145160 A1 | 8/2017 | |

OTHER PUBLICATIONS

Laura M. Ensign, Craig Schneider, Jung Soo Suk, Richard Cone, and Justin Hanes. "Mucus Penetrating Nanoparticles: Biophysical Tool and Method of Drug and Gene Delivery." Advanced Materials, vol. 24, 2012, pp. 3887-3894. (Year: 2012).*

Hirofumi Takeuchi, Hiromitsu Yamamoto, and Yoshiaki Kawashima. "Mucoadhesive nanoparticulate systems for peptide drug delivery." Advanced Drug Delivery Reviews 47 (2001) pp. 39-54. (Year: 2001).*

Bandar E. Al-Dhubiab, Anroop B. Nair, Rachna Kumria, Mahesh Attimarad, and Sree Harsha. "Development and evaluation of buccal films impregnated with selegiline-loaded nanospheres." Drug Delivery, 2016; 23(7), pp. 2154-2162. (Year: 2016).*

K. Yoncheva, E. Lizarraga, J.M. Irache, "Pegylated nanoparticles based on poly(methyl vinyl ether-co-maleic anhydride): preparation and evaluation of their bioadhesive properties." European Journal of Pharmaceutical Sciences, vol. 24, 2005, pp. 411-419 (9 pages).

Singh, Inderbir et al., "Exploiting the interaction of polymethacrylates with iron oxide for the enhancement of mucoadhesive strength," Pak. J. Pharm. Sci., vol. 27, No. 2., Mar. 2014, pp. 343-350 (8 pages).

Polymeric Biomaterials: Structure and Function, vol. 1, CRC Press, 2013, pp. 193-220 (32 pages).

P.R. Karn, Z. Vanic, I. Pepic, and N. Skalko-Basnet, "Mucoadhesive liposomal delivery systems: the choice of coating material." Drug Development and Industrial Pharmacy, vol. 37(4), 2011, pp. 482-488 (7 pages).

G. Yosipovitch, I. Kaplan, S. Calderon, M. David, Y.H. Chan, A. Weinberger, "Distribution of Mucosal pH on the Bucca, Tongue, Lips and Palate." Acta Dermatologica Venereologica, vol. 81, 2001, pp. 178-180 (3 pages).

J.O. Morales, J.T. McConville, "Manufacture and characterization of mucoadhesive buccal films," European Journal of Pharmaceutics and Biopharmaceutics, vol. 77, 2011, pp. 187-199 (13 pages).

Z. Cui, R.J. Mumper, Bilayer Films for Mucosal (Genetic) Immunization via the Buccal Route in Rabbits, Pharmaceutical Research, vol. 19, No. 7, Jul. 2002, pp. 947-953 (7 pages).

N. Salamat-Miller, M. Chittchang, T.P. Johnston, The use of mucoadhesive polymers in buccal drug delivery, Advanced Drug Delivery Reviews, vol. 57, 2005, pp. 1666-1691 (26 pages).

* cited by examiner

FILM DOSAGE FORM WITH EXTENDED RELEASE MUCOADHESIVE PARTICLES

CROSS-REFERENCE TO RELATED APPLICATIONS

This application is a continuation-in-part of U.S. application Ser. No. 15/588,897, filed May 8, 2017, which claims priority to U.S. application Ser. No. 14/554,332, filed Nov. 26, 2014 (now U.S. Pat. No. 9,668,970), and which claims benefit of U.S. Provisional Application No. 61/910,604, filed Dec. 2, 2013, and which are hereby incorporated by reference in their entireties.

FIELD OF THE DISCLOSURE

This disclosure relates generally to controlled release oral dosage forms, especially those oral film dosage forms releasing an active agent over a sustained period of time.

BACKGROUND OF THE DISCLOSURE

Film dosage forms that provide extended release of an active agent have been known. Such film dosage forms are known to comprise at least two layers, which include at least one mucoadhesive layer to facilitate adhesion of the dosage form to mucosa for an extended period, and a layer that acts as a diffusion barrier that prevents or restricts loss of the active agent from the dosage form to saliva in the oral cavity and ultimately to the gastrointestinal tract. The active agent can be located in the mucoadhesive layer or in a third, reservoir layer between the mucoadhesive layer and the diffusion barrier layer. Such multiple layer film dosage forms require preparation of multiple formulations, casting of multiple film layers, and combining the multiple layers into a composite, such as by casting one layer on another layer, or using a lamination process. As a result, multiple layer film dosage forms for achieving sustained release of an active agent for local delivery in the buccal cavity can be difficult and expensive to produce. Multiple-layer, sustained-release film oral dosage forms can also be undesirable to some patients, as the film dosage form must be retained in the oral cavity for an extended period, all the while providing a palpable sensation that many patients find undesirable. In addition, swelling of the mucoadhesive film, may also present an important source of discomfort to the patient.

It has been suggested that mucoadhesive particles can be incorporated into oral dosage forms such as capsules, cachets, pills, tablets, lozenges, powders, granules, syrups or liquid suspensions to facilitate transport of an active agent across mucosal barriers.

It has also been suggested that mucoadhesive particles can be incorporated into ophthalmic suspensions or administered rectally, parenterally, intracistemally, intravaginally, intranasally, intraperitoneally, topically, buccally or in an oral or nasal spray.

SUMMARY OF THE DISCLOSURE

The disclosed dosage forms facilitate controlled (e.g., sustained) release of an active agent for local delivery in the buccal cavity, and transport through oral mucosa, while avoiding the discomfort associated with long lasting mucoadhesive films or tablets that must typically reside on the oral mucosa during the period of controlled release. Controlled release of an active agent for local action in the buccal cavity in accordance with the disclosed dosage form is achieved by providing a dosage form in which mucoadhesive particles of a small size (e.g., from several nanometers to several micrometers), which contain the active agent, are dispersed in a disintegrating film. Upon administration in the oral cavity, the film disintegrates (e.g., within an acceptable period of time) and releases the mucoadhesive particles, some of which will contact the oral mucosa and immediately become tenaciously bound to the mucosa. The active agent can be released from the mucoadhesive particles over a prolonged period of time as the mucoadhesive material slowly dissolves or erodes.

In certain disclosed embodiments, the mucoadhesive particles are comprised of a mucoadhesive, non-biodegradable polymer such as polyacrylic acid or a copolymer of maleic anhydride and a methylvinyl ether, maleic acid and a methylvinyl ether or polymethacrylates-based copolymers.

In certain disclosed embodiments, the mucoadhesive particles are comprised of a mucoadhesive biodegradable polymer such as poly-(D,L-lactide-co-glycolide).

In certain disclosed embodiments, the mucoadhesive particles are made of an oil particle with a polymer material located at the interface of the oil particle or surrounding it. This oil particle, containing the active agent, is also comprised of an oil base, one or more surfactants, a permeation enhancer, and an antioxidant.

The disclosed dosage forms include those having a single layer comprising the active agent-containing mucoadhesive particles dispersed in a disintegrating film.

The disclosed dosage forms can comprise at least two layers, including at least one layer formed from mucoadhesive particles dispersed in a distinguishing film and at least one layer formed from a mucoadhesive, non-mucoadhesive or controlled release composition.

The disclosed dosage forms may comprise a single active agent that is present in only the mucoadhesive particles or in both the mucoadhesive particles and in any of a free form dispersed in the disintegrating film, in a granular, enterically coated, or other controlled release form that is dispersed in the disintegrating film along with the mucoadhesive particles or that is dispersed in a different film of a multiple layer dosage form.

The disclosed dosage forms providing transport of an agent for local delivery in a buccal cavity of a subject for a sustained period of time, may comprise a disintegrable film matrix; and mucoadhesive particles dispersed in the disintegrable film, the particles comprising a mucoadhesive material exhibiting adhesivity to the mucosa in the buccal cavity and/or to the gastrointestinal tract and at least a first active agent, wherein the disintegratable film has a disintegrating time within which 90% of the film is disintegrated, and wherein the mucoadhesive particles have a modulated erosion time within which 90% of the mucoadhesive material encapsulating the active agent is dissolved in the buccal fluid.

The disclosed dosage forms may deliver active agent locally in the buccal cavity for the topical treatment of a disease arising in the oral cavity.

The disclosed dosage forms may be used for mucosal delivery of vaccines to induce immune responses at both systemic and mucosal sites or to prevent invasion and colonization of pathogens at mucosal surfaces. In this case, the film conveniently delivers a vaccine using needle-free vaccine approach.

The disclosed dosage forms may comprise active agents capable of being absorbed transmucosally such as active agents that are permeable to the buccal mucosa. Buccally permeable active agents are generally small molecules which are soluble and permeable. Buccally permeable active agent are generally classified as class I active agents according to the Biopharmaceutical Classification System.

The disclosed dosage form may also comprise non-permeable active agents or active agents that are only permeable over a prolonged period of time. These active agents are thus preferably administered with a permeation or penetration enhancer. However, since the oral film matrix quickly disintegrates, a penetration enhancer dispersed in the film matrix would simply be swallowed with little effect other than possibly promoting some penetration of active agent comprised in the film matrix but not (or to very little extent) the active agent comprised within the mucoadhesive particles. For the penetration enhancer to increase permeation of active agent encapsulated in the mucoadhesive particles, the permeation enhancer can be included in the mucoadhesive particles. Disclosed is an oral film dosage form providing transport of an agent for delivery in the buccal cavity for buccal absorption, the oral film dosage form comprising a disintegrable film and mucoadhesive particles comprising mucoadhesive material encapsulating an active agent and a penetration enhancer.

The disclosed dosage forms providing transport of an agent for local delivery in a buccal cavity of a subject for at least two different agents for a sustained period of time, may comprise a disintegrable film matrix, first mucoadhesive particles dispersed in the disintegrable film, the first mucoadhesive particles comprising a mucoadhesive material exhibiting adhesivity to mucosa in the buccal cavity and a first active agent that is released over a sustained period and second mucoadhesive particles dispersed in the disintegrable film, the second mucoadhesive particles comprising a mucoadhesive material that is different from the first mucoadhesive material, exhibiting adhesivity to mucosa in the buccal cavity that is different from the first mucoadhesive particles and a second active agent that is released over a sustained period from the second mucoadhesive particles, wherein the first mucoadhesive particles have a first erosion time within which at least 90% of the mucoadhesive material is dissolved or dispersed and the second mucoadhesive particles have a second erosion time within which 90% of the mucoadhesive material is dissolved or dispersed, and wherein the first 90% erosion time is different from the second 90% erosion time.

These and other features, advantages and objects of the various embodiments will be better understood with reference to the following specification and claims.

DETAILED DESCRIPTION OF THE DISCLOSED EMBODIMENTS

The disclosed orally administrable dosage forms can be used to provide sustained release of an agent that is delivered for local action anywhere in the buccal cavity or under the tongue. The dosage forms can be employed in a variety of treatments in which release of a particular active agent in the buccal cavity or under the tongue over a prolonged period of time provides a beneficial effect. Examples include treatment of gingivitis, buccal ulcers, canker sores, Sjögren's syndrome, oral mucositis, and Behçet's disease.

According to certain embodiments, the sustained release dosage forms are also suitable for mucosal delivery of vaccines, which in comparison to injectable vaccines may lead to significantly fewer side effects and exclude the possibility of needle borne infections and pain at the site of injection during and after the injection. Additionally, the increased residence time of the vaccine antigen at the mucosal surfaces may enhance the uptake of antigen by mucosal antigen-reactive immune cells.

According to certain embodiments, the sustained release dosage forms are also suitable for active agents with low permeation capability. Increasing the residence time of the active agent within the oral cavity through the mucoadhesion of the particles, particularly with mucoadhesive particles having an erosion time greater than that of mucoadhesive oral film, allows active agents having low permeation to be permeable to the buccal mucosa and exhibit improved transmucosal absorption. An example of active agents requiring increased residence time is tetrahydrocannabinol and its derivatives such as dronabinol.

In certain aspects or embodiments of this disclosure, the film matrix in which the mucoadhesive particles are dispersed is non-mucoadhesive or low-mucoadhesive (substantially less mucoadhesive than the mucoadhesive particles). Preferably, the non-mucoadhesive or substantially less mucoadhesive film matrix quickly disintegrates in the oral cavity when exposed to saliva allowing the liberated mucoadhesive particles to freely attach to oral mucosal tissue. The non-mucoadhesive films are designed to disintegrate or dissolve in the oral cavity without adhering to oral mucosal surfaces. The film matrices that are substantially less mucoadhesive than the mucoadhesive particles are not capable of being retained on an oral mucosal surface for a prolonged period and adhere, if at all, to such mucosal surfaces less strongly than the mucoadhesive particles. The polymer components of the non-mucoadhesive and low-mucoadhesive films are comprised entirely or mostly (e.g., at least 60% by weight, 70% by weight, 80% by weight or 90% by weight) of water soluble polymers that are not specially identified as mucoadhesive materials.

Sustained release delivery of an agent for local delivery in the buccal cavity is achieved with a dosage form that is essentially imperceptible to the patient. Rather than leaving a mucoadhesive film or patch of substantial size on the oral mucosa during the duration of the extended treatment, the active agent is released from mucoadhesive particles that are adhered to oral mucosa and are of a size that is essentially unnoticeable to the patient. The term "particle" refers to a nanoscopic (1 to 1000 nm) or microscopic (1 to 1000 micrometers) solid or semi-solid aggregate structures. The particles can be spherical or non-spherical (e.g., ellipsoidal or rod-like) structures, with hollow or solid core, such as solid spheres, micelles, vesicles, liposomes or lamellaes. For example, it is possible to employ known techniques to form mucoadhesive particles comprising a mucoadhesive material and an active agent that have a particle size range from a few nanometers (e.g., 5 nm, 10 nm, 50 nm, 100 nm) to a few micrometers (e.g., 1 µm, 100 µm, 200 µm, 300 µm, 500 µm).

The term "bioadhesion" and "bioadhesivity" generally mean a material that tends to adhere to living tissue to facilitate prolonged retention at a site of application. A mucoadhesive material is a bioadhesive material that can interact with mucus or a mucosal surface and thereby provide prolonged retention of a drug at a mucosal surface as compared with a simple liquid or powder system that does not include a bioadhesive material.

In order to reduce patient discomfort and facilitate rapid adhesion or bioadhesion between the mucoadhesive particles and oral mucosa (e.g., buccal mucosa), the mucoadhesive particles are distributed in a disintegrating film. In certain embodiments, the film disintegrates completely without leaving a noticeable residue. As the film disintegrates, the mucoadhesive particles are released, with those contacting oral mucosa immediately and tenaciously bonding to the mucosa.

In the case where particular areas of the buccal mucosa are targeted for treatment, the dosage form can be placed immediately adjacent or in contact with the targeted mucosa. For example, a dosage form used to treat a canker sore on buccal mucosa can be positioned directly on the sore to promote disintegration of the film and adhesion of the residual mucoadhesive particles.

The term "disintegrating" and variations thereof generally refers to the ability of the film dosage forms to break up into particles and/or dissolve within an acceptable period of time (e.g., within less than 5 minutes, within 4 minutes, within 3 minutes, within 2 minutes, or within 1 minute or within 15 to 30 seconds of being administered, (i.e., placed in the oral cavity of a subject). A "disintegrating time within which 90% of the film is disintegrated" ("90% disintegration") means that time at which the largest part of a film submerged in a simulated saliva solution comprises 10% of the weight of the original film before it is contacted with the simulated saliva (an aqueous solution buffered to a pH of about 6.7 to 7.4).

Disintegrating films suitable for use in preparing the disclosed dosage forms are typically comprised of at least one water soluble polymer. In certain embodiments, the disintegrating film does not include insoluble polymers or other materials that can leave a gritty, unpleasant residue. Surfactants, polyalcohols, and or plasticizers may be incorporated into the disintegrating film to facilitate or enhance wettability and disintegration of the film.

Water soluble polymers that can be employed in the disclosed films include water soluble cellulose derivatives, including hydroxypropylmethyl cellulose, hydroxyethyl cellulose, hydroxypropyl cellulose; polyvinyl pyrrolidone (PVP); copovidone (a copolymer of 1-vinyl-2-pyrrolidone and vinyl acetate); other copolymers of vinyl pyrrolidone; other polymers or copolymers of substituted vinyl pyrrolidone; derivatives of polyvinyl pyrrolidone; polyethylene oxide, carboxymethyl cellulose; polyvinyl alcohol; natural gums, including xanthan, tragacanth, guar, acacia and arabic gums; and water soluble polyacrylates. Combinations of these water soluble polymers or other water soluble polymers can also be used. Examples of substituted vinyl pyrrolidones include N-vinyl-3-methyl-2-pyrrolidone, N-vinyl-4-methyl-2-pyrrolidone, N-vinyl-5-methyl-2-pyrrolidone, N-vinyl-5,5-dimethyl-2-pyrrolidone, N-vinyl-3,3,5-trimethyl-2-pyrrolidone and others. Examples of monomers that can be copolymerized with vinyl pyrrolidone or substituted vinyl pyrrolidones include vinyl aromatic monomers such as styrene, and acrylate or methacrylate monomers such as methyl methacrylate and 2-dimethylaminoethyl methacrylate.

The terms "surfactant" and "polyalcohol" are intended to have their ordinary meanings. Specifically, the term "surfactant" is intended to mean an amphiphilic compound that lowers the surface tension of a liquid, the interfacial tension between two liquids, or the interfacial tension between a liquid and a solid. Examples of surfactants that can be used in a disintegrating film of an oral dosage form are known and include polyoxy-ethylene sorbitan fatty acid esters, an α-hydro-co-hydroxypoly (oxyethylene) poly (oxypropylene) poly(oxyethylene) block copolymer, a polyoxyethylene allyl ether, a polyoxyethylene, a phospholipid or a castor oil derivative. Combinations of surfactants can be used. The term "polyalcohol" means a sugar alcohol, which is a hydrogenated form of a carbohydrate having a carbonyl group that has been reduced to a primary or secondary hydroxyl group. Polyalcohols are also distinguishable based on their chemical formula. Polyalcohols have the general formula $H(HCHO)_{n+1}H$, whereas sugars have the general formula $H(HCHO) HCO$. Common examples of polyalcohols or sugar alcohols that can be used from the disclosed films include glycol, glycerol, erythritol, threitol, arabitol, xylitol, ribitol, mannitol, sorbitol, galactitol, fucitol, iditol, inositol, volemitol, isomalt, maltitol, lactitol, maltotritol and maltotetraitol.

The term "penetration enhancer" as used herein to describe and claim the invention refers to a substance that can increase buccal permeation of an active ingredient by enabling a transcellular route for transportation of the drug through the buccal epithelium. Certain non-limiting examples of pharmaceutically acceptable penetration enhancers include benzalkonium chloride, cetylpyridinium chloride, cyclodextrins, dextran sulfate, lauric acid/propylene glycol, menthol, oleic acid, oleic acid derivatives, polyoxyethylene, polysorbates (such as Polysorbate 80), sodium EDTA, sodium lauryl sulfate, sodium salicylate.

In certain embodiments, the disclosed films may include a plasticizer. The term "plasticizer" refers to a component that reduces the glass-transition temperature of the film forming polymers (e.g., the water soluble polymer or water soluble polymers in the film). The plasticizer increases the flexibility, enhances elasticity and reduces brittleness of the film. Examples of plasticizers that can be used in the disclosed film oral dosage forms include polyethylene glycol, triacetin, triethyl citrate, tributyl citrate, acetyl tributyl citrate, acetyl triethyl citrate, trioctyl citrate, acetyl trioctyl citrate, trihexyl citrate, dibutyl sebacate, glycerol etc. Plasticizer may be added in an amount up to 25% of the total mass of the film oral dosage form, such as from 0.5% to 25%, 1% to 20%, 2% to 15% or 5% to 10%.

Optionally, an active agent can be incorporated into the disintegrating film in an immediate release form (i.e., a form that is not incorporated into sustained release mucoadhesive particles), such as in a free particulate form or immediate release granular form. The agent incorporated into the disintegrating film in an immediate release form can be the same agent as in the mucoadhesive particles or a different agent.

The term "agent" and "active agent" refer to any agent that is being administered orally to a subject and includes pharmaceutically active agents, nutraceutically active agents, vaccine antigens, flavoring agents, and breath freshening agents. Examples of pharmaceutically active agents include ACE-inhibitors, antianginal drugs, anti-arrhythmics, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, live-attenuated viruses, inactivated viruses, virus like particles, vaccine antigens, antibodies, enzymes, antigens, acne drugs, alkaloids, amino acid preparations, anti-tussives, anti-uricemic drugs, anti-viral drugs, anabolic preparations, systemic and non-systemic anti-infective agents, anti-fungal agents, anti-neoplastics, anti-parkinsonian agents, antirheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, erectile dysfunction therapies such as sildenafil citrate, tadalafil, and vardenafil, fertility agents, gastrointestinal agents, homeopathic remedies, hormones, hypercalcemia and hypocalcemia management agents, immunomodulators, immunosuppressives, anti-migraine preparations such as rizatriptan, eletriptan and zolmitriptan, motion sickness treatments, muscle relaxants, obesity management agents, osteoporosis preparations, oxytocics, parasympatholytics, parasympathomimetics, prostaglandins, psychotherapeutic agents, respiratory agents, sedatives such as lorazepam or diazepam, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents such as alprazolam, anti-ulcer agents, anti-inflammatory substances, coronary dilators, cerebral dilators, peripheral vasodilators, psycho-tropics, stimulants, anti-hypertensive drugs, vasoconstrictors, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-astmatics, cough suppressants, mucolytics, DNA and genetic modifying drugs, and combinations thereof. Examples of nutraceutically active agents include various dietary supplements, vitamins, minerals, herbs and nutrients. Breath freshening agents include, for example, spearmint oil, cinnamon oil, peppermint oil, clove oil, menthol, etc.

Compositions suitable for mucosal delivery of vaccines can comprise a live-attenuated virus, inactivated virus, or a virus like particle used as vaccines or as delivery vehicles. For example, the mucoadhesive particles can incorporate virus vaccines including, but not limited to, Picornaviruses (e.g., polio virus, foot and mouth disease virus), Caliciviruses (e.g., SARS virus, and feline infectious peritonitis virus), Togaviruses (e.g., sindbis virus, the equine encephalitis viruses, chikungunya virus, rubella virus, Ross River virus, bovine diarrhea virus, hog cholera virus), Flaviviruses (e.g., dengue virus, West Nile virus, yellow fever virus, Japanese encephalitis virus, St. Louis encephalitis virus, tick-borne encephalitis virus), Coronaviruses (e.g., human coronaviruses (common cold), swine gastroenteritis virus), Rhabdoviruses (e.g., rabies virus, vesicular stomatitis viruses), Filoviruses (e.g., Marburg virus, Ebola virus), Paramyxoviruses (e.g., measles virus, canine distemper virus, mumps virus, parainfluenza viruses, respiratory syncytial virus, Newcastle disease virus, rinderpest virus), Orthomyxoviruses (e.g., human influenza viruses, avian influenza viruses, equine influenza viruses), Bunyaviruses (e.g., hantavirus, LaCrosse virus, Rift Valley fever virus), Arenaviruses (e.g., Lassa virus, Machupo virus), Reoviruses (e.g., human reoviruses, human rotavirus.), Birnaviruses (e.g., infectious bursal virus, fish pancreatic necrosis virus), Retroviruses (e.g., HIV 1, HIV 2, HTLV-1, HTLV-2, bovine leukemia virus, feline immunodeficiency virus, feline sarcoma virus, mouse mammary tumor virus), Hepadnaviruses (e.g., hepatitis B virus), Parvoviruses (e.g., human parvovirus B, canine parvovirus, feline panleukopenia virus) Papovaviruses (e.g., human papillomaviruses, SV40, bovine papillomaviruses), Adenoviruses (e.g., human adenovirus, canine adenovirus, bovine adenovirus, porcine adenovirus), Herpes viruses (e.g., herpes simplex viruses, varicella-zoster virus, infectious bovine rhinotracheitis virus, human cytomegalovirus, human herpesvirus 6), and Poxviruses (e.g., vaccinia, fowlpoxviruses, raccoon poxvirus, skunkpox virus, monkeypoxvirus, cowpox virus, musculum contagiosum virus).

In some embodiments, the active agent incorporated into mucoadhesive particles in the disintegrating film is the same in each mucoadhesive particle. In other aspects, the film may comprise mucoadhesive particles, which incorporate different active agents.

The total amount of agent(s) that can be incorporated in the disintegrating films disclosed herein is generally from 0.01% to 80% by total weight of the film, such as 1% to 60%, 2% to 50%, or 5% to 40% by total weight of the film.

The term "matrix" or "film matrix" refers to the polymer component or mixture of polymers, which creates the film forming matrix supporting the API within the oral film dosage form. The mucoadhesive particles are dispersed within the film matrix.

The disclosed oral film dosage form may have various weight ratios of film/particles. The film/particles weight ratios may vary depending on the active agent. The film/particles weight ratio is typically in the range of about 1 to about 100, preferably in the range of from about 5 to about 75, and more preferably in the range of from about 10 to about 50. In other words, the disclosed oral film dosage forms have a film matrix that is about 1 to about 100 times, preferably about 5 to about 75 times, and more preferably about 10 to about 50 times the weight of the particles.

Examples of mucoadhesive materials that can be used to prepare the mucoadhesive particles include poly(ethylene oxide), polyvinyl pyrrolidone, poly(acrylic acid) derivatives (e.g., commercially available Carbopol®, and Pemulen®, the latter being a copolymer of acrylic acid and alkyl acrylate crosslinked with allyl pentaerythritol), polycarbophil polymers, polyoxyalkylene ethers, polymethacrylates, polymethacrylates-based copolymers (e.g., commercially available Eudragit®), biodegradable polymers such as poly (D,L-lactide-co-glycolide) (e.g., commercially available Resomer®), anionic biopolymers such as hyaluronic acid, or sodium carboxymethylcellulose, cationic biopolymers such as chitosan or poly(L-lysine) and other cellulose derivatives. Other mucoadhesive polymers that can be used include methyl vinyl ether-maleic acid, a mixed salt of sodium/calcium methyl vinyl ether-maleic acid, methyl vinyl ether-maleic anhydride, and half esters (monoethyl; monobutyl and isopropyl ester) of methyl vinyl ether-maleic anhydride copolymers (e.g., commercially available Gantrez®).

Additional suitable mucoadhesive materials may be chosen from the group consisting of alginate, pectin, chitosan, hyaluronic acid (and esters thereof), agar agarose, dextran, ovalbumin, collagen casein and copolymers of glycolide-based monomers.

The agent incorporated into the mucoadhesive particles can be any of the previously listed active agents that can optionally be added, along with the mucoadhesive particles, to the disintegrating film in immediate release form or in a controlled release form that is not incorporated into a mucoadhesive.

Examples of agents that can be beneficially employed in the mucoadhesive particles are those for treating fungal or bacterial infections, gingivitis, buccal ulcers, canker sores, Sjögren's syndrome, oral mucositis, Behçet's disease or other conditions that can be beneficially treated from long exposure or controlled release (e.g., sustained release) of an agent for local delivery in the buccal cavity. Systemic treatments where there is a pronounced food effect or the bioavailability of the active product or for active products that need to be absorbed in the upper gastrointestinal tract could also benefit from use of the disclosed dosage forms.

Particular categories of agents that can be incorporated into the mucoadhesive particles include antimicrobial agents including antibacterial agents and/or antifungal agents, such as triclosan, chlorhexidine, doxycycline, tetracycline, minocycline, neomycin, caspofungin, miconazole, micafungin, and anidulafungin; topical analgesic agents such as benzydamine, amlexanox, lidocaine and diclofenac; corticosteroid anti-inflammation agents such as hydrocortisone, beclomethasone dipropionate, clobetasol, betamethasone sodium phosphate, and dexamethasone; agents for modulating immune response such as prednisolone, colchicines, pentoxifylline, azothioprine, thalidomide, dapsone, mycophenolate, mofetil, adalimumab, vitamin B12, clofazimine, fevamizole, montelukast, and sulodexide; and disease modifying antirheumatic agents, such as methotrexate and hydroxychloroquine. These and other agents can be used alone or in combination, either incorporated into the disintegrating film in an immediate release form or non-mucoadhesive controlled release form, in the mucoadhesive particles, or both.

As a specific example, for the treatment of canker sores, an antimicrobial agent and a topical analgesic agent may be used together in the mucoadhesive particles to provide simultaneous treatment and relief from pain. Alternatively, or in addition, the topical analgesic agent can be incorporated as an immediate release agent in the disintegrating film. As another example, Sjogren's disease can be treated with a combination of cevimeline and/or pilocarpine, and optionally with a corticosteroid anti-inflammatory agent and/or a disease-modifying antirheumatic agent, which optional agents can be added in a free form to the film, to the mucoadhesive particles, or both to the mucoadhesive particles and in free form to the film.

According to certain embodiments, the disclosed oral film dosage form, comprises particles that are mucoadhesive. Mucoadhesive particles as opposed to mucoadhesive film or tablet, may allow the film to be quickly disintegrated and/or dissolved and swallowed while the mucoadhesive particles remain in the buccal cavity, preferably adhered to the oral mucosa, thus removing discomfort generally felt from administration of known mucoadhesive dosage forms in which the entire film adheres to the mucosa for a prolonged period of time (residence time).

According to certain embodiments of the present disclosure, the disclosed oral film dosage form may be suitable for both buccal and enteral delivery. The delivery of the API will thus vary depending on the method of administration of the oral film dosage form. This innovative mucoadhesive dosage form thus potentially allows two alternative routes of administration using a single oral dosage form. In such an embodiment, the delivery of the API will be dependent on the method of administration of the oral film dosage form.

According to certain embodiments, the oral film dosage form may be administered for buccal delivery. When administered for buccal delivery of the active agent, the film is administered to the patient in a way that promotes film disintegration in close proximity to the oral mucosa. For instance, the film administered for buccal delivery may be given to a patient with the indication of being positioned against the oral mucosa inside the cheeks or under the tongue (administered sublingually). Therefore, once disintegrated, the mucoadhesive particles adhere to the mucosa and remain there for a specific residence time. The residence time of the mucoadhesive particles being substantially affected by their dissolution rate (also referred to as the erosion time), the quantity of saliva present in the mouth, and the size of the mucoadhesive particles. The faster the dissolution of the mucoadhesive particle the shorter the residence time and conversely, the longer the dissolution time, the greater the residence time. The extent to which the active agent is released from the particles may be modulated by the use of various mucoadhesive or polymer materials generally having distinct mucoadhesive properties or distinct viscosity and solubility, hence having different dissolution rates in saliva and consequently, different residence times. The term "erosion time within which 90% of the mucoadhesive material is dissolved" (or "90% erosion time") refers to the time in which 90% of the weight of the mucoadhesive particles are dissolved after being submerged in simulated saliva (buffered to a pH of about 6.7 to 7.4). Such 90% erosion time is expected to be representative of, and approximately equal to the residence time or 90% erosion time in the buccal cavity of a human subject in the absence of food consumption and rinsing.

For certain embodiments, it may be desired to have an oral film dosage form wherein two active agents are retained (and respectively released) for different periods of time.

Where the disclosed oral dosage form is used for local delivery, according to such certain embodiments, the mucoadhesive particles containing the active agent have the potential to alleviate the symptoms or provide other therapeutic effect over a longer period of time than other known systemic administration techniques for the same active agent. The increased residence time of the active agent in the oral cavity may continuously dispense (or release) the active agent locally over an extended period of time. In addition, the disclosed oral film may continuously dispense (or release) active agents without the discomfort usually felt from comparable mucoadhesive dosage forms (films or tablets) where the dosage form itself is mucoadhesive. The presently disclosed dosage form having mucoadhesive particles as opposed to having a mucoadhesive matrix typically allows adherence of the particles to the mucosa without being an inconvenience for the patient.

According to certain embodiments, the oral film dosage form may be administered for enteral delivery. In such embodiment, the oral film is administered in a way that promotes quick disintegration of the film followed by swallowing of the mucoadhesive particles. For instance, the oral film may be positioned on the tongue where the disintegrating film will be swallowed and the mucoadhesive particles contained therein will be delivered to the stomach thus potentially adhering to the enteral mucosa. Additional indications could include the intake of water and/or food shortly after administration of the film on the tongue to promote swallowing of the mucoadhesive particles destined for enteral delivery.

Contrary to known mucoadhesive oral dosage forms, the disclosed oral dosage forms in certain embodiments can be suitable for both buccal and enteral delivery depending on the prescribing information and its mode of administration. The mucoadhesive particles of the presently described oral dosage forms are delivered via the film matrix which by design disintegrates in the oral cavity upon contact with saliva. It is thus possible to modulate the administration of the active agent contained within the mucoadhesive particle depending on the ailment or disease in need of treatment. The disclosed oral dosage forms may thus be used for treating both local disease, such as disease located in a patient's mouth as well as treatment of disease systemically wherein the active agent is administered to the patient enterally and/or buccally and reaches the bloodstream.

According to certain other embodiments, the disclosed oral dosage form is designed for administration of active agents both buccally and enterally. In such embodiment, the oral dosage form is administered to a patient with specific prescribing information to have a portion of the film positioned on either the buccal or sublingual mucosa and another portion of the same film dosage form positioned on the tongue for disintegration and quick swallowing of the disintegrated film portion. Similarly, the prescribing information may require the patient to take two distinct oral films each being applied against a different portion of the oral cavity. For instance, a first oral film may be applied sublingually while the second oral film is applied against the mucosa or where enteral absorption is desired the second film is positioned on the tongue for quick dissolution and swallowing of the mucoadhesive particles.

Alternatively, according to certain other embodiments where the oral dosage form is designed for both buccal and enteral delivery, the oral film may comprise two forms of the active agent, a first form positioned in the film via the use of mucoadhesive particles and a second form disposed in the film without the use of mucoadhesive particles. In such embodiments, disintegration of the film leaves both the first and second form of active, with and without mucoadhesive particles, dispersed in the saliva. The suspended mucoadhesive particles would generally adhere to the mucosa whereas the remaining active which is dispersed in the film matrix in a non-mucoadhesive format would generally be swallowed and reach the bloodstream via the typical enteral delivery route. Quick disintegration of the film and comparatively quick swallowing of the suspended active agent may also affect absorption of the active agent, thus favoring quicker absorption of the non-mucoadhesive active agent.

According to some other embodiments, the oral dosage form is designed for the treatment of both local and systemic administration. As such, the oral dosage form allows quick administration of the active agent transmucosally bypassing the first pass mechanism while the remaining mucoadhesive particles (the swallowed particles) are administered enterally.

Based on the type of material used a wide range of erosion times may be achieved (few minutes up to few days, for instance, from about 300 seconds to about 3 to 5 days). In addition, it is possible to tune or modulate the overall physical properties of the polymer-drug matrix by controlling the relevant parameters such as polymer molecular weight (10 kDa up to 5000 kDa), ratio of monomers or co-monomers (25:75, 50:50; 75:25) and drug concentration (0.1 to 20%) to achieve a desired dosage and release interval depending upon the drug type or active agent used.

Examples of biodegradable materials that can be used to create mucoadhesive particles with tunable erosion or dissolving time include polysaccharides (starch, chitosan/chitin, gums, pectins), proteins (gelatin, collagen, casein), polyhydroxyalkanoates (PHA), polyhydroxybutyrate (PHB), polyhydroxybutyrate co-hydroxyvalerate (PHBV), polylactides (polylactic acid (PLA), polylactic-co-glycolic acid (PLGA), polycaprolactones (polyesters PCL).

The residence time of the mucoadhesive particles is affected by several parameters. These parameters may be used for modulation of the residence time of mucoadhesive particles and thus affect the extended release profile of the active agent. For a defined mucoadhesive material, the size of mucoadhesive particles and molecular size and/or molecular weight of the mucoadhesive material directly affects the mucoadhesive particles erosion time and are important parameters used to modulate the residence time of the mucoadhesive particles in the oral cavity and/or in the GIT. The larger the mucoadhesive particles, the longer they will generally adhere to the mucosa and thus the longer the buccal and/or GIT residence time. Conversely, the smaller the mucoadhesive particles the faster they will dissolve and the smaller their buccal or enteral residence time will be. Other factors, such as food consumption and rinsing of the mouth may affect the residence time of the mucoadhesive particles particularly the residence time in the buccal cavity.

According to certain embodiments, having mucoadhesive particles as opposed to having a mucoadhesive film matrix generally allows the active agent to be released over a longer period of time compared with the same active agent being delivered through known mucoadhesive oral films where the film matrix itself is mucoadhesive. The overall increased surface area contact of multiple released mucoadhesive particles with the oral mucosa compared to a single oral film also allows the particles to adhere to the oral mucosa in greater frequency and for an increased period of time (residence time of the active in the oral cavity) when compared to known mucoadhesive films. In addition, the mucoadhesive particles have the ability to deposit active for applications such as local treatment over a larger mucosal surface area than ordinary film dosage forms that do not have the mucoadhesive particles. The conventional film would only deliver where positioned in the mouth, whereas the mucoadhesive particles will move until adhered to the surface and will be able to cover area other than where the film was placed, delivering the active in a more distributed manner where desired.

According to certain embodiments, the mucoadhesive particles have an erosion time within which 90% of the mucoadhesive material is dissolved that is typically from five to five thousand times the disintegrating time within which 90% of the film is disintegrated.

According to certain embodiments, the oral film dosage form is used to deliver orally active agents that are permeable to the buccal mucosa. Transmucosal absorption of the active agent is generally affected by the permeation of the active agent through the mucosa and by the erosion time of the mucoadhesive particles which in most cases is directly related to the rate of release of the active agent.

Active agents which are permeable through the oral or buccal mucosa are generally low molecular weight, neutral molecules, generally classified as class I according to Biopharmaceutics Classification System (BCS). BCS is a system to differentiate the drugs on the basis of their solubility and permeability. This system is limited by its ability to group actives using only two parameters, the active solubility and its intestinal permeability. The solubility classification is based on a United States Pharmacopoeia (USP) aperture. Class II molecules are highly soluble and highly permeable however, enteral permeation is not indicative that the molecule will be buccally permeable. Other factors such as molecule size and the charge of the molecule may affect its permeation.

In such embodiments, as the film disintegrates the mucoadhesive particles will adhere to the buccal mucosa. The retention time in the buccal cavity will depend on the time required by the mucoadhesive particles to erode (erosion time). During retention in the buccal cavity, the active agent can diffuse into the mucosa or be released by erosion. Released active agent is, to a significant extent, absorbed transmucosally through penetration of the buccal mucosa.

According to certain embodiments, the oral film dosage form is used to deliver an active agent that has low permeation to the buccal mucosa.

According to an aspect of the disclosure, the microparticles may be passively targeted to antigen-presenting cells (APCs) in mucosal membranes such as macrophages and dendritic cells. The ability of APCs to phagocytose particulates is dependent on the particle size. In particular, about 1.0 to about 10.0 m diameter microspheres are optimally taken up by APCs.

According to an aspect of the disclosure, microparticles are also designed to target other membrane-proteins in the mucosa, or other motif in the oral cavity such as lesions, cuts or sores.

According to certain embodiments, the disclosed oral film dosage form is designed to administer active agents capable of transmucosal absorption through the buccal mucosa. In such embodiments, the mucoadhesive particles allow the active agent to be absorbed through the oral mucosa over a prolonged period of time. This extended release of the active agent is achieved via the longer residence time of the particles in the oral cavity. According to this embodiment, extended release and absorption is dependent on the ability of the active agent to traverse the mucosa and be absorbed transmucosally. The disclosed oral dosage form for providing transport of an agent for local delivery in a buccal cavity of a subject for a sustained period of time, comprises a disintegrable film and mucoadhesive particles dispersed in the disintegrable film, the particles comprising a mucoadhesive material exhibiting adhesivity to mucosa in the buccal cavity and at least a first active agent capable of being absorbed transmucosally.

According to certain embodiments, the disclosed oral film dosage form is designed to enhance transbuccal administration of an active agent which is weakly permeable to the buccal mucosa. In such embodiments, a penetration enhancer is employed, preferably a penetration enhancer that is administered conjointly or simultaneously available with the active agent. Adding a penetration enhancer to a film matrix will only potentially improve the penetration of active agent which is instantly released with the disintegration of the matrix (not the active contained in the mucoadhesive particles). Penetration enhancer available instantly following the disintegration of the matrix will thus not significantly improve the permeation of the active agent released over a sustained period of time. In other words, the active agent contained in the mucoadhesive particles will not benefit from an immediate release (at the time of the disintegration of the film matrix) of the penetration enhancer. In accordance with these certain embodiments, enhanced transbuccal delivery of an active agent is achieved by incorporating a penetration enhancer, along with the active agent, within the mucoadhesive particles.

The oral dosage form according to these embodiments will be made by a process that differs from the other embodiments in that the permeation enhancer will be added to the mucoadhesive particles. One way to include the penetration enhancer in the mucoadhesive particles is by adding the penetration enhancer to a liquid phase in which the active agent is dissolved and which is used in the preparation of the mucoadhesive particles (such as by solvent displacement technique or emulsification technique, described herein). Using this process, both the active agent and the permeation enhancer will be encapsulated in the mucoadhesive material thus creating the mucoadhesive particles.

Similar to embodiments previously described, certain embodiments comprising more than one active agent may include a combination of active agents which are buccally permeable to different degrees. For instance, embodiments of the oral film dosage form may comprise a first active agent that is permeable to the buccal mucosa and a second active that is not permeable to the buccal mucosa. Transbuccal delivery of the second active agent can be enhanced with a penetration enhancer. The penetration enhancer can be added to the same portion of the film where the second active is. For example, in an oral film where a first active agent having low permeation to buccal mucosa is instantly released, a penetration enhancer and the first active agent can be added to the film matrix for instant delivery as the film matrix disintegrates while a second active agent can remain in the mucoadhesive particles for delivery over a prolonged period of time. Conversely, for an oral film where the non- or weakly permeable active agent is administered over a prolonged period of time, a first active agent (the permeable one) will be added to the film matrix for delivery instantly as the film disintegrates in the buccal cavity while a second active will be encapsulated in the mucoadhesive material with a penetration enhancer.

Other embodiments could also comprise a plurality of active agents that are not permeable or only weakly permeable. In such embodiments, all active agents can be administered with a penetration enhancer. As such, a penetration enhancer could be added to both the film matrix and the mucoadhesive particles.

According to some embodiments, the mucoadhesive particles may have residence times lasting from about 5 min to a few days (e.g., 2 to 3 days), depending on the size of the mucoadhesion particles and the mucoadhesive materials used. The erosion time and thus the residence time of the mucoadhesive particles is related to the molecular weight and other physical and/or chemical properties of the mucoadhesive material.

The disclosed oral film dosage form systems comprise a disintegrating matrix and mucoadhesive particles containing the active agent. The present system may thus be modulated for various residence times according to the desired treatment and the active agent effectiveness. The residence time in the oral cavity of the mucoadhesive particle will be modulated by various parameters such as size of the mucoadhesive particles, the materials used in the mucoadhesive particles, and pH of the medium.

In some embodiments, the particles are formed using precipitation techniques, followed by coating of the particles with a block copolymer. Precipitation techniques (e.g., microprecipitation techniques, nanoprecipitation techniques) may involve forming a first solution comprising the polymeric material (or other hydrophobic material) and a solvent, wherein the polymeric material is substantially soluble in the solvent. The solution may be added to a second solution comprising another solvent in which the polymeric material is substantially insoluble, thereby forming a plurality of particles comprising the polymeric material. In some cases, one or more surfactants, and/or bioactive agents may be present in the first and/or second solution.

In some embodiments, the particles are mesoporous material covered in mucoadhesive polymers that slowly dissolve to release API at a controlled rate from the meso porous material. A mesoporous material is a material containing pores with diameters between 2 and 50 nm. Silica is an example of a mesoporous material.

In an exemplary embodiment, a method of forming the particles includes using a poly(ethylene glycol)-vitamin E conjugate (hereinafter "PEG-VitE conjugate" or "VPSk"). The PEG-VitE conjugate can act as a surfactant, may aid in stabilizing the particles, and/or may aid in encapsulating the particle material. In some cases, a method for forming a plurality of particles using PEG-VitE comprises forming a solution comprising a hydrophobic polymeric material (or other hydrophobic material), and adding the solution to a solvent in which the hydrophobic material is substantially insoluble. The PEG-VitE conjugate may be present in the solution comprising the hydrophobic material and/or the solvent to which the solution is present. Upon addition of the solution comprising the hydrophobic material to the solvent, a plurality of particles form, which are stabilized by the PEG-VitE conjugate. The PEG-VitE conjugate may be present in the solvent or solution at about 0.1%, 0.5%, 1.0%, 1.5%, 1.65%, 2%, 3%, 4%, 5%, 10%, 20% weight percent, or greater. Examples of solvents that may be suitable in this method include, but are not limited to, acetonitrile, benzene, p-cresol, toluene, xylene, mesitylene, diethyl ether, glycol, petroleum ether, hexane, cyclohexane, pentane, dichloromethane (methylene chloride), chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like.

Another technique that may be used for preparing the mucoadhesive particles is a solvent displacement technique.

Solvent displacement method is based on spontaneous emulsification of an organic internal phase (i.e., acetone, ethanol, or butyl alcohol alone or as a mixture), also referred to as the solvent phase, into an aqueous (mainly water) or hydroalcoholic external phase (alcohol/water mixture).

The solvent phase is a solution of a polymer (e.g., Eudragit® family (polymethacrylates-based copolymers), Resomer® family (such as poly(D,L-lactide-co-glycolide), or Gantrez® family (copolymer of maleic anhydride)) and the active substance (e.g., antifungal, antibacterial, gingival treatments, buccal ulcer treatments, canker sore treatments) in an organic solvent miscible with water.

The polymer and the active substance are dissolved in a water-miscible solvent of intermediate polarity, leading to precipitation of the particles. This phase is transferred into a stirred aqueous or hydroalcoholic solution optionally in the presence of a stabilizing surfactant. Polymer deposition on the interface between the water and the organic solvent, caused by fast diffusion of the solvent, leads to the instantaneous formation of a colloidal suspension.

It is possible to use either two organic phases or two aqueous phases or mixtures thereof as long as solubility, insolubility and miscibility conditions are satisfied. Regarding particle preparation, the organic phase is mixed with the stirred aqueous phase in one shot, stepwise, dropwise or other controlled addition. The organic solvent is removed from the system using evaporation under reduced pressure.

Alternatively, the mucoadhesive particles can be prepared by single or multiple emulsification techniques. The organic inner phase is a solution of the polymer in the presence or absence of the active substance in an organic solvent system (e.g., ethyl acetate, isobutyl acetate, methyl ethyl ketone (MEK), dichloromethane (DCM), or ethyl formate alone or in combination) partially miscible or non-miscible with the outer phase (water or silicone oil). The outer phase can be saturated with an organic solvent. It is possible for some active substances to be dissolved first in an aqueous phase and then emulsified in an organic partially miscible solvent phase to form the first microemulsion droplet, and then emulsified within the outer phase. The outer phase comprises the dispersion of a stabilizing agent (e.g., polyvinyl alcohol (PVA), polysorbates) or sodium lauryl sulfate prepared by using solvent-saturated phase.

Optionally, a cross-linking agent can be used during the production of the mucoadhesive particles to improve their stability and extend the residence time. Examples of cross-linking agents that may be suitable for use in the invention include, but are not limited to, acetate salts such as magnesium or calcium acetate, carbodiimide and diamine compounds or their derivatives.

For both techniques, the mucoadhesive particles are formed instantaneously with a size range between 100 nm and 100 m depending on the operating conditions. The operating conditions can be varied to obtain specific particle compositions, morphologies and sizes, and improve the local extended residence time.

The two methods allow active substance loading ranges between 0.5-20% and entrapment efficiencies ranges between 50 and 99.9%.

Production of Antimicrobial Drug Loaded Gantrez AN Mucoadhesive Particles

Solvent displacement method: 20 mg of antimicrobial drug are dissolved in 5 ml of Gantrez AN/organic phase solution at 2% w/v. The mucoadhesive particles are produced by the addition of 20 ml of hydroalcoholic solution (1:1) under stirring for 10 min at 4° C. The alcohol is removed under reduced pressure using a rotary evaporator. The aqueous suspension of drug loaded Gantrez particles are collected and used in the formulation of water soluble films.

Emulsification method: 20 mg of antimicrobial drug are dissolved in 5 ml of Gantrez AN/MEK solution at 2% w/v. The organic phase (O) is emulsified in an aqueous/PVA solution (W) using a high speed homogenizer for 5 min. to achieve an oil-in-water emulsion system. If necessary, the organic solvent is removed by extraction/evaporation or filtration technique. The drug loaded Gantrez particles are collected and used in the formulation of water soluble films.

Production of Viral Vaccine-Loaded Mucoadhesive Particles

100 µL of Minimal Essential Medium containing a single vaccine dosage is slowly added into a 500 µL organic solution of methylene chloride/ethanol/isopropanol (1:3:1 volume ratio) and mixed by vortexing. This mixture is emulsified by vortexing in a 5 mL aqueous solution containing 50 mg sodium alginate, 12.5 mg PVA (124-186 kDa) and 12.5 mg citric acid. The temperature during vortexing is kept between 10 and 25° C.

Production of Film Oral Dosage Form

The mucoadhesive particles, sweetener, flavor and a pore former are combined in water and stirred until a homogeneous dispersion (wet-blend) is obtained. Polyethylene oxide is then added gradually to the wet blend and mixed until the polyethylene oxide is completely dissolved. The wet blend is then coated on support liner and dried in an oven until the moisture level reaches between about 2% to about 10%, preferably less than 5%. The obtained product is cut to a desired size and packaged. Pore former are generally understood agent that aid, promote or speed up the disintegration time of the film in the oral cavity. A pore former is an agent such as maltodextrin that quickly dissolves on the surface of the film, creating holes which allow water to enter the film and thus promote film dissolution and/or disintegration.

Conventional mixing techniques can be employed for dispersing the mucoadhesive particles and other optional active agents into the film composition, which typically comprises a suitable solvent, and contains any optional ingredients such as plasticizers, polyalcohols, and surfactants. The film composition containing the mucoadhesive particles and any optional active agents present in either a free, immediate release form, or in a non-mucoadhesive controlled release form can be cast and dried to form a film using known processes.

Preparation of Films Through Low Temperature Drying

In certain embodiments it would be preferable to manufacture an oral film at lower temperatures to prevent the API or agent such as biological molecules like peptides, proteins, enzymes, nucleosides, nucleotides, antigen or modified/natural DNA/RNA, from degradation. In general, once an oral film is cast on a liner it enters a series of ovens at elevated temperatures selected to achieve a target residual moisture, yielding a dry film that is not brittle and easy for packaging processing. Depending on the sensitivity of the API or biological agent this drying process can be modified to achieve low or high temperature drying as well as any intermediate range. A high temperature drying process, greater than 55° C., will involve the wet product moving through the oven quickly, with a lower residence time. Conversely, a low temperature drying process, below 55° C., will involve the wet product moving through the oven much more slowly, with a longer residence time. In this way even temperature sensitive agents such as vaccines can readily be incorporated into an oral film and manufactured large scale.

In certain embodiment films, temperature sensitive active or solutions such as vaccine may be produced through quick pass high temperature coating. In the very expeditious or quick pass coating, the high temperature oven used to dry the films is desired to obtain a dry product while minimizing the heat exposure of the active. This high temperature quick pass coating process relies on the fact that the active is only exposed to high temperature for a very short period, which is dependent on the heat stability of the active or active solution (i.e. vaccine). The heat exposition period need to be short enough in duration to prevent unacceptable degradation of the active.

In certain embodiment films intended to deliver temperature sensitive API or agents may be prepared through a dry casting method. In these samples a wet blend is first prepared containing the API or agent, this blend is then pour into a cast or mold and allowed to air dry over 24-72 hours. This allows the water or solvent to evaporate from the mixture and the film forming excipients deposit and dry into a finished product without the use of heating.

Production of THC/CBD Film Oral Dosage Form

A mucoadhesive particle containing an active agent as a *cannabis* extract, *cannabis* oil, tetrahydrocannabinol (THC), THC complexated with cyclodextrin (CD), cannabidiol (CBD), or a THC/CBD combination of variable composition, is prepared by an emulsification technique.

The active cannabinoid agent is added to the oil phase containing an oil base, one or more surfactants, and an antioxidant. The aqueous phase is comprised of an emulsifier, one or more surfactants, an antibacterial, a flavoring agent, and a mucoadhesive polymer. Both phases are mixed together using a high-speed homogenizer to achieve an oil-in-water emulsion blend system.

A mucoadhesive polymer or a combination of mucoadhesive polymers is added to the oil-in-water emulsion blend until complete solubilzation of the polymers. The blend is coated on a liner and dried in an oven at a temperature below 60° C. The obtained film is then cut and packaged.

In certain embodiments, a mucoadhesive polymer or a combination of mucoadhesive polymers is dissolved in the aqueous phase before addition of the oil phase, followed by preparation of the oil-in-water emulsion blend.

In certain embodiments, the disclosed particles may include an oil base. The term "oil base" refers to the main component of the oil particle, found in the highest amount. The other components would be dissolved or dispersed in this oil base. Examples of this oil base include fats and oils of different melting points, such as soybean oil, sesame oil, coconut oil, sunflower oil, cocoa butter, palm oil, palm kernel oil, caprylic/capric triglyceride, carnauba wax, beeswax, or paraffin wax.

A flavoring agent is used to modify and enhance the taste of the resultant film. Flavoring oils and oleoresins might be added to the oil phase. Examples of these are natural essential oils like peppermint oil, cinnamon oil, *eucalyptus* oil, orange oil, spearmint oil, or lemon oil. Synthetic flavoring substances, such as vanillin, DL-menthol, eugenol, or limonene, can be added to either the oil or the aqueous phase depending on their solubility.

In certain embodiments, polyethylene oxide is premixed and added together with other polymers. Polyethylene oxide contributes to the stability of the oil-in-water emulsion during mixing of the blend and drying of the film. Consequently, no oil is found at the surface of the final film product.

Example of emulsification procedure: 0.7 g of THC are dissolved into 10 g of soybean oil, together with 0.01 g of α-tocopherol and 4 g of oleic acid. Simultaneously, 1.4 g of poloxamer 188, 0.7 g of soy lecithin, 1.6 g of polyethylene glycol, 0.2 g of methylparaben, 0.4 g of DL-menthol, and 3 g of hydroxypropyl cellulose are dissolved or dispersed in 100 mL of water. The oil phase is emulsified in the aqueous phase by using a high-speed homogenizer for 5 min to achieve an oil-in-water emulsion.

Example of emulsification procedure: 0.6 g of THC are dissolved into 8 g of coconut oil, together with 0.01 g of butylated hydroxytoluene and 3.4 g of oleic acid. Simultaneously, 1.1 g of poloxamer 407, 0.6 g of soy lecithin, 2.6 g of glycerol, 1.5 g of sucralose, 0.2 g of methylparaben, and 3 g of hydroxypropyl cellulose are dissolved or dispersed in 100 mL of water. The oil phase is emulsified in the aqueous phase by using a high-speed homogenizer for 5 min to achieve an oil-in-water emulsion.

Example of emulsification procedure: 0.7 g of *cannabis* oil is added to 10 g of melted cocoa butter. Also, 0.01 g of butylated hydroxytoluene, 0.7 g of soy lecithin, and 1 g of peppermint oil are added to the oil base. Simultaneously, 2.6 g of glycerol, 1.5 g of sucralose, and 0.2 g of methylparaben are dissolved or dispersed in 100 mL of water, also warmed up to 60° C. The oil phase is emulsified in the aqueous phase by using a high-speed homogenizer for 5 min to achieve an oil-in-water emulsion.

Example of emulsification procedure: 0.7 g of THC and 4.3 g of cyclodextrin (CD) are mixed in 7 ml of ethanol to form a THC/CD complex. The complex in ethanol is dispersed in 10 g of soybean oil, together with 0.01 g of α-tocopherol and 4 g of oleic acid. Simultaneously, 1.4 g of poloxamer 188, 0.7 g of soy lecithin, 1.6 g of glycerol, 0.2 g of methylparaben, 0.4 g of DL-menthol, and 3 g of hydroxypropyl cellulose are dissolved or dispersed in 100 mL of water. The oil phase is emulsified in the aqueous phase by using a high-speed homogenizer for 5 min to achieve an oil-in-water emulsion.

Example of emulsification procedure: 1 g of *cannabis* oil is mixed with 2.5 g mint oil emulsified with 1.25 g of polysorbate 85 until a homogenous oil mixture is formed. This oil mixture is added to an aqueous solution containing 0.25 g citric acid, 0.3 g sucralose, 0.8 g sorbitol, and 70 g of water. The resulting oil/water solution is mixed with a high-speed homogenizer for 5 min to achieve an oil-in-water emulsion.

The resultant emulsion is mixed with 20 g of a high molecular weight hydroxypropyl cellulose until the polymer completely dissolve. The blend is coated on a liner and dried in an oven at 40° C.

Alternatively, the high molecular weight polymer is 22 g pullulan premixed with 0.15 g xanthan gum, 0.15 g locust bean gum, and 1.0 g carrageenan.

Example of emulsification procedure and film preparation: 2 g of glycerol, 2 g of polyethylene glycol, 1.5 g of sucralose, 0.2 g of methylparaben, 15 g of hydroxypropyl cellulose, 5 g of hydroxypropylmethyl cellulose, and 2 g of polyethylene oxide are dissolved or dispersed in 100 mL of water. Afterwards, 0.6 g of THC are dissolved into 8 g of soybean oil, together with 0.01 g of tocopherol, 0.2 g of peppermint oil, and 0.3 g of Pemulen. The oil phase is then added into the aqueous phase while mixing for 60 minutes through agitation until obtaining an oil-in-water emulsion blend, which is cast on a liner and dried.

According to one embodiment, the oral film dosage form comprises THC, CBD or a combination thereof encapsulated within mucoadhesive particles. According to other embodiments, the oral film dosage form comprises a first active (either THC, CBD or a combination of cannabinoids) and a second non cannabinoid active, wherein at least one of the first and second active is comprised within mucoadhesive particle.

According to one embodiment, the oral film comprises mucoadhesive particles having a microencapsulated THC-cyclodextrin complex or cannabinoid-cyclodextrin complex. According to one embodiment, the complex is gamma-cyclodextrin-THC.

According to one embodiment, the process for making a cannabinoid oral film comprises the steps of blending cannabinoid emulsion with high molecular weight cellulose, coating the blend as a thin sheet on a liner and drying the coated blend at a temperature below 60° C. or preferably at a temperature below about 40° C.

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. An oral film dosage form providing transport of an active agent for local delivery in a buccal cavity of a subject for a sustained period of time, comprising:
   (a) a disintegrable film; and
   (b) solid polymer particles dispersed in the disintegrable film, the particles comprising a mucoadhesive material exhibiting adhesivity to mucosa in the buccal cavity, wherein the active agent is contained in the solid polymer particles, and the active agent is a *cannabis* extract, *cannabis* oil, synthetic tetrahydrocannabinol (THC), THC purified from *cannabis* extract, THC complexated with cyclodextrin (CD), cannabidiol (CBD), or a THC/CBD combination.

2. The oral film dosage form of claim 1, wherein the mucoadhesive particles have an erosion time within which 90% of the mucoadhesive material is dissolved.

3. The oral film dosage form of claim 2, wherein the 90% erosion time is from about 15 seconds to about 300 seconds.

4. The oral film dosage form of claim 1, wherein the mucoadhesive material is taken from the group consisting of polysaccharides, proteins, polyhydroxyalkanoates (PHA), polyhydroxybutyrate (PHB), polyhydroxybutyrate co-hydroxyvalerate (PHBV), polylactides and polycaprolactones (polyesters PCL).

5. The oral film dosage form of claim 1, wherein the mucoadhesive material is selected from poly(ethylene oxide), polyvinyl pyrrolidone, poly (alkyl acrylates), poly (alkyl methacrylates), polycarbophils, polyoxyalkylene ethers, poly (D,L-lactide-co-glycolide), carboxymethylcellulose, chitosan and poly(L-lysine).

6. The oral film dosage form of claim 1, wherein the solid polymer particles further comprise an oil taken from the group consisting of soybean oil, sesame oil, coconut oil, sunflower oil, cocoa butter, palm oil, palm kernel oil, caprylic/capric triglyceride, carnauba wax, beeswax, and paraffin wax.

7. The oral film dosage form of claim 1, wherein the solid polymer particles have sizes of between about 1.0 μm to about 10.0 μm diameter for mucosal uptake delivery.

8. An oral film dosage form providing transport of an agent for local delivery in a buccal cavity of a subject for at least two different agents for a sustained period of time, comprising:
   (a) a disintegrable film;
   (b) first solid polymer particles dispersed in the disintegrable film, the first solid polymer particles comprising a first mucoadhesive material exhibiting adhesivity to mucosa in the buccal cavity and a first active agent contained in the first solid polymer particles for release over a sustained period from the first mucoadhesive material; and
   (c) second solid polymer particles dispersed in the disintegrable film, the second solid polymer particles comprising a second mucoadhesive material exhibiting adhesivity to mucosa in the buccal cavity that is different from the first mucoadhesive material and a second active agent contained in the second solid polymer particles that is the same as or different from the first active agent and is released over a sustained period from the second mucoadhesive material, wherein at least one of the first and second active agents is a *cannabis* extract, *cannabis* oil, tetrahydrocannabinol (THC), THC complexed with cyclodextrin (CD), cannabidiol (CBD), or a THC/CBD combination.

9. The oral film dosage form of claim 8, wherein the first mucoadhesive material has a first 90% erosion time and second mucoadhesive material has a second 90% erosion time, and wherein the first 90% erosion time is different from the second 90% erosion time.

10. The oral film dosage form of claim 9, wherein the second erosion time is between 1.0 and 20 times the first erosion time.

11. The oral film dosage form of claim 9, wherein the first 90% erosion time is between about 300 seconds and 3 days.

12. The oral dosage form of claim 8, wherein the first mucoadhesive material is taken from the group consisting of chitosan, polyvinyl pyrrolidone, alginate, polycarbophil, pectin, hyaluronic acid and esters thereof, agar agarose, dextran, ovalbumin, collagen, and casein.

13. The oral film dosage form of claim 8, wherein the first mucoadhesive material is taken from the group consisting of polysaccharides, proteins, polyhydroxyalkanoates (PHA), polyhydroxybutyrate (PHB), polyhydroxybutyrate co-hydroxyvalerate (PHBV), polylactides, and polycaprolactones.

14. The oral film dosage form of claim 8, wherein at least one of the first and second mucoadhesive materials is selected from poly(ethylene oxide), polyvinyl pyrrolidone, poly (alkyl acrylates), poly (alkyl methacrylates), polycarbophils, polyoxyalkylene ethers, poly (D,L-lactide-co-glycolide), carboxymethylcellulose, chitosan and poly(L-lysine).

15. The oral film dosage form of claim 14, wherein at least one of the first and second mucoadhesive materials further comprises an oil taken from the group consisting of soybean oil, sesame oil, coconut oil, sunflower oil, cocoa butter, palm oil, palm kernel oil, caprylic/capric triglyceride, carnauba wax, beeswax, and paraffin wax.

16. The oral film dosage form of claim 15, wherein at least one of the first and second solid polymer particles have sizes of between about 100 nm and about 100 micrometers.

17. The oral film dosage form of claim 16, wherein at least one of the first and second solid polymer particles have sizes of between about 1.0 µm to about 10.0 µm diameter for mucosal uptake delivery.

18. The oral film dosage form of claim 15, wherein the weight ratio of film/particles is in the range of from 10 to 50.

19. An oral dosage form providing transport of an agent for transmucosal local delivery in a buccal cavity of a subject for a sustained period of time, comprising:
   (a) a disintegrable film matrix; and
   (b) solid polymer particles dispersed in the disintegrable film matrix, the particles comprising a mucoadhesive material exhibiting adhesivity to mucosa in the buccal cavity and at least a first active agent contained in the mucoadhesive particles,
   wherein the first active agent is capable of being absorbed transmucosally through the buccal mucosa, and wherein the disintegrable film matrix exhibits lower mucoadhesivity than the mucoadhesive particles.

20. The dosage form of claim 19, wherein said solid polymer particles further comprise at least one penetration enhancer selected from benzalkonium chloride, cetylpyridinium chloride, cyclodextrins, dextran sulfate, lauric acid/propylene glycol, menthol, oleic acid, oleic acid derivatives, polyoxyethylene, polysorbates, sodium EDTA, sodium lauryl sulfate, and sodium salicylate.

* * * * *